(12) United States Patent
Schroeder

(10) Patent No.: US 12,714,001 B2
(45) Date of Patent: Aug. 25, 2026

(54) AGRICULTURAL SYSTEM AND METHOD FOR MONITORING SOIL MOISTURE WITHIN A FIELD DURING THE PERFORMANCE OF AN AGRICULTURAL OPERATION

(71) Applicant: CNH Industrial America LLC, New Holland, PA (US)

(72) Inventor: Brittany Schroeder, Bunker Hill, IN (US)

(73) Assignee: CNH Industrial America LLC, New Holland, PA (US)

( * ) Notice: Subject to any disclaimer, the term of this patent is extended or adjusted under 35 U.S.C. 154(b) by 957 days.

(21) Appl. No.: 17/941,732

(22) Filed: Sep. 9, 2022

(65) Prior Publication Data

US 2024/0085347 A1 Mar. 14, 2024

(51) Int. Cl.
*A01B 79/00* (2006.01)
*A01B 63/00* (2006.01)
(Continued)

(52) U.S. Cl.
CPC .......... *A01B 79/005* (2013.01); *G01N 22/04* (2013.01); *G01N 33/24* (2013.01); *G01N 33/246* (2013.01);
(Continued)

(58) Field of Classification Search
CPC ...... G01N 22/04; G01N 33/246; G01N 33/24; G01N 33/42; G01N 33/245; A01B 63/008; A01B 79/005; A01B 47/00
(Continued)

(56) References Cited

U.S. PATENT DOCUMENTS 6,937,939 B1 * 8/2005 Shibusawa .......... G01N 33/246 356/336
9,675,004 B2 6/2017 Landphair et al.
(Continued)

FOREIGN PATENT DOCUMENTS

CN 111163629 A 5/2020
DE 102019217555 B4 * 1/2022 .......... B60W 40/04
(Continued)

OTHER PUBLICATIONS

Coutinho, R. M., Sousa, A., Santos, F., & Cunha, M. (May 28, 2022). "Contactless Soil Moisture Mapping Using Inexpensive Frequency-Modulated Continuous Wave Radar for Agricultural Purposes". Applied Sciences,  12(11), 5471. https://doi.org/10.3390/app12115471 (Year: 2022).*
(Continued)

*Primary Examiner* — Ramon A. Mercado
*Assistant Examiner* — Moya Ly
(74) *Attorney, Agent, or Firm* — Dority & Manning, P.A.

(57) ABSTRACT

A system for monitoring soil moisture within a field during the performance of an agricultural operation with an agricultural implement includes a first soil moisture sensor spaced apart from the field, a second soil moisture sensor supported on the agricultural implement and being of a different sensor type from the first soil moisture sensor, and a computing system that selects a first predetermined relationship associated with an expected soil type at a first location and determines a first moisture content at the first location based on data from the first soil moisture sensor and the first predetermined relationship. Moreover, the computing system determines a second moisture content at the first location based on data from the second soil moisture sensor. Additionally, the computing system determines whether the first predetermined relationship is associated with an actual
(Continued)

300

302 — SELECTING A FIRST PREDETERMINED RELATIONSHIP FROM A PLURALITY OF PREDETERMINED RELATIONSHIPS, EACH OF THE PLURALITY OF PREDETERMINED RELATIONSHIPS BEING ASSOCIATED WITH DETERMINING A MOISTURE CONTENT FOR A RESPECTIVE SOIL TYPE OF A PLURALITY OF SOIL TYPES, THE FIRST PREDETERMINED RELATIONSHIP BEING ASSOCIATED WITH AN EXPECTED SOIL TYPE AT A FIRST LOCATION WITHIN A FIELD

304 — RECEIVING FIRST DATA INDICATIVE OF THE SOIL MOISTURE WITHIN THE FIELD, THE FIRST DATA BEING GENERATED BY A FIRST SOIL MOISTURE SENSOR, THE FIRST SOIL MOISTURE SENSOR BEING A NON-CONTACT SENSOR SPACED APART FROM THE FIELD

306 — DETERMINING A FIRST MOISTURE CONTENT INDICATIVE OF THE SOIL MOISTURE AT THE FIRST LOCATION OF THE AGRICULTURAL IMPLEMENT WITHIN THE FIELD BASED AT LEAST IN PART ON THE FIRST PREDETERMINED RELATIONSHIP AND THE FIRST DATA

308 — RECEIVING SECOND DATA INDICATIVE OF THE SOIL MOISTURE WITHIN THE FIELD, THE SECOND DATA BEING GENERATED BY A SECOND SOIL MOISTURE SENSOR SUPPORTED ON AN AGRICULTURAL IMPLEMENT PERFORMING AN AGRICULTURAL OPERATION WITHIN THE FIELD, THE SECOND SOIL MOISTURE SENSOR BEING OF A DIFFERENT TYPE THAN THE NON-CONTACT SENSOR

310 — DETERMINING A SECOND MOISTURE CONTENT INDICATIVE OF THE SOIL MOISTURE AT THE FIRST LOCATION BASED AT LEAST IN PART ON THE SECOND DATA

312 — DETERMINING WHETHER THE FIRST PREDETERMINED RELATIONSHIP IS ASSOCIATED WITH AN ACTUAL SOIL TYPE AT THE FIRST LOCATION BASED AT LEAST IN PART ON THE FIRST MOISTURE CONTENT AND THE SECOND MOISTURE CONTENT soil type at the first location based on the first and second moisture contents.

15 Claims, 5 Drawing Sheets

(51) Int. Cl.
*G01N 22/04* (2006.01)
*G01N 33/24* (2006.01)
*A01B 47/00* (2006.01)

(52) U.S. Cl.
CPC ............. *A01B 47/00* (2013.01); *A01B 63/008* (2013.01); *G01N 33/245* (2024.05)

(58) Field of Classification Search
USPC ............................................................ 701/50
See application file for complete search history.

(56) References Cited

U.S. PATENT DOCUMENTS

| | | | | |
|---|---|---|---|---|
| 9,804,113 | B2 | 10/2017 | Kumaran et al. | |
| 10,073,074 | B1 | 9/2018 | Kumar et al. | |
| 10,145,837 | B2 | 12/2018 | Troxler | |
| 10,175,218 | B2 * | 1/2019 | Visser | G01N 21/359 |
| 10,416,106 | B1 | 9/2019 | Pruessner | |
| 11,185,009 | B2 | 11/2021 | Maxton et al. | |
| 11,346,832 | B2 | 5/2022 | Koch et al. | |
| 2003/0009286 | A1 * | 1/2003 | Shibusawa | A01B 79/005 702/2 |
| 2009/0302870 | A1 | 12/2009 | Paterson et al. | |
| 2015/0028890 | A1 | 1/2015 | Troxler | |
| 2017/0090068 | A1 * | 3/2017 | Xiang | G01N 33/0098 |
| 2021/0026007 | A1 | 1/2021 | Ferrari | |
| 2021/0195821 | A1 * | 7/2021 | Knobloch | A01B 47/00 |
| 2021/0341407 | A1 * | 11/2021 | Burkey | G01N 27/223 |
| 2022/0022365 | A1 | 1/2022 | Finlay et al. | |

FOREIGN PATENT DOCUMENTS

| | | | |
|---|---|---|---|
| WO | WO 2020/160605 | A1 | 8/2020 |
| WO | WO 2021/144629 | A1 | 7/2021 |

OTHER PUBLICATIONS

"Contactless Soil Moisture Mapping Using Inexpensive Frequency-Modulated Continuous Wave Radar for Agricultural Purposes" Rui M. Coutinho, et al. Applied Sciences Article May 28, 2022 (15 pages) https://www.mdpi.com/2076-3417/12/11/5471/pdf?version=1653966187.

"Calibration of Capacitive Soil Moisture Sensor (SKU:SEN0193)" Radi, et al. 2018 4$^{th}$ International Conference on Science and Technology (ICST) Yogyakarta, Indonesia 2018 (6 pages) https://sci-hub.hkvisa.net/10.1109/ICSTC.2018.8528624.

"Calibration and Validation of a Low-Cost Capacitive Moisture Sensor to Integrate the Automated Soil Moisture Monitoring System" Ekanayaka Achchillage Ayesha Dilrukshi Nagahage, et al. Agriculture Technical Note Graduate School of Science and Engineering Saitama University Sakura-ku, Saitama, Japan Jul. 4, 2019 (10 pages) https://sci-hub.hkvisa.net/10.3390/agriculture9070141.

"Sensing Methodologies in Agriculture for Soil Moisture and Nutrient Monitoring" Bhuwan Kashyap, et al. IEEE Access Invited Paper vol. 9 Jan. 18, 2021 (27 pages) https://ieeexplore.ieee.org/stamp/stamp.isp?arnumber=9328258.

* cited by examiner

AGRICULTURAL SYSTEM AND METHOD FOR MONITORING SOIL MOISTURE WITHIN A FIELD DURING THE PERFORMANCE OF AN AGRICULTURAL OPERATION

FIELD OF THE INVENTION

The present disclosure relates generally to agricultural implements and, more particularly, to monitoring soil moisture within a field during the performance of agricultural operations with agricultural implements.

BACKGROUND OF THE INVENTION

It is well known that, to attain the best agricultural performance from a field, a farmer must cultivate the soil, typically through a tillage operation. Tillage implements typically include a plurality of ground engaging tools configured to engage the soil as the implement is moved across the field. Such ground engaging tool(s) loosen and/or otherwise agitate the soil up to a certain depth in the field to prepare the field for subsequent agricultural operations, such as planting operations.

When performing a tillage operation, it is desirable to create a level and uniform layer of tilled soil across the field to form a proper seedbed in subsequent planting operations. However, due to varying soil conditions across the field, particularly soil moisture content, tillage conditions such as the levelness of the tillage floor, compaction, and/or the like of the tillage layer may be impacted significantly if the implement is not properly adjusted for such varying soil conditions. Poor tillage conditions can result in losses in crop yield. For example, if soil is very wet, and an operating depth of tillage tools of the implement is not properly adjusted, the tools may begin to plug, which may cause the soil to be compacted by the tillage tools. Soil compaction may cause a hard pan or soil crust within the soil profile to form as the soil dries, which hinders crop root growth and prevents proper water infiltration, therefore causing losses in crop yield.

Ground-penetrating radar (GPR) may be used to generate GPR data indicative of different field characteristics, including soil moisture content, of a field. However, the GPR data must be assessed in view of the soil type (e.g., based on soil composition and/or texture) of the field being analyzed, as dissipation of the energy from the GPR sensor changes based on soil type. Typically, soil type maps, such as Soil Survey Geographic (SSURGO) maps, may be pre-generated for the field and used to assess the GPR data. However, the soil type maps may not be precise, as the sensors used to collect the soil type map data may have an accuracy or resolution range within a few meters and/or the frequency for collecting data points may be low. As such, the moisture content determined for a particular location in the field based on the GPR data generated by the GPR sensor and the soil type determined from the pre-generated may not be accurate, particularly at transitions between different soil types in the field.

Accordingly, an improved agricultural system and method for monitoring soil moisture within a field during the performance of agricultural operation with an agricultural implement would be welcomed in the technology.

BRIEF DESCRIPTION OF THE INVENTION

Aspects and advantages of the invention will be set forth in part in the following description, or may be obvious from the description, or may be learned through practice of the invention.

In one aspect, the present subject matter is directed to an agricultural system for monitoring soil moisture within a field during the performance of an agricultural operation with an agricultural implement. The agricultural system may include a first soil moisture sensor configured to generate first data indicative of soil moisture within the field, with the first soil moisture sensor being a non-contact sensor spaced apart from the field during the agricultural operation. The agricultural system may further include a second soil moisture sensor configured to generate second data indicative of soil moisture within the field, where the second soil moisture sensor is supported on the agricultural implement, and where the second soil moisture sensor being of a different sensor type from the first soil moisture sensor. Additionally, the agricultural system may include a computing system communicatively coupled to the first and second soil moisture sensors. The computing system may be configured to select a first predetermined relationship from a plurality of predetermined relationships, with each of the plurality of predetermined relationships being associated with determining a moisture content for a respective soil type of a plurality of soil types, and with the first predetermined relationship being associated with an expected soil type at a first location within the field. Further, the computing system may be configured to determine a first moisture content indicative of the soil moisture at the first location based at least in part on the first data and the first predetermined relationship. Moreover, the computing system may be configured to determine a second moisture content indicative of the soil moisture at the first location based at least in part on the second data. Additionally, the computing system may be configured to determine whether the first predetermined relationship is associated with an actual soil type at the first location based at least in part on the first moisture content and the second moisture content.

In another aspect, the present subject matter is directed to an agricultural method for monitoring soil moisture within a field during the performance of an agricultural operation with an agricultural implement. The method may include selecting, with a computing system, a first predetermined relationship from a plurality of predetermined relationships, where each of the plurality of predetermined relationships is associated with determining a moisture content for a respective soil type of a plurality of soil types, and where the first predetermined relationship being associated with an expected soil type at a first location within the field. The method may further include receiving, with the computing system, first data indicative of the soil moisture within the field, with the first data being generated by a first soil moisture sensor, and with the first soil moisture sensor being a non-contact sensor spaced apart from the field. Further, the method may include determining, with the computing system, a first moisture content indicative of the soil moisture at the first location of the agricultural implement within the field based at least in part on the first predetermined relationship and the first data. Furthermore, the method may include receiving, with the computing system, second data indicative of the soil moisture within the field, with the second data being generated by a second soil moisture sensor supported on the agricultural implement, and with the second soil moisture sensor being of a different sensor type from the first soil moisture sensor. Moreover, the method may include determining, with the computing system, a second moisture content indicative of the soil moisture at the first location based at least in part on the second data. Additionally, the method may include determining, with the computing system, whether the first predetermined relationship is associated with an actual soil type at the first location based at least in part on the first moisture content and the second moisture content.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

Figure 1:
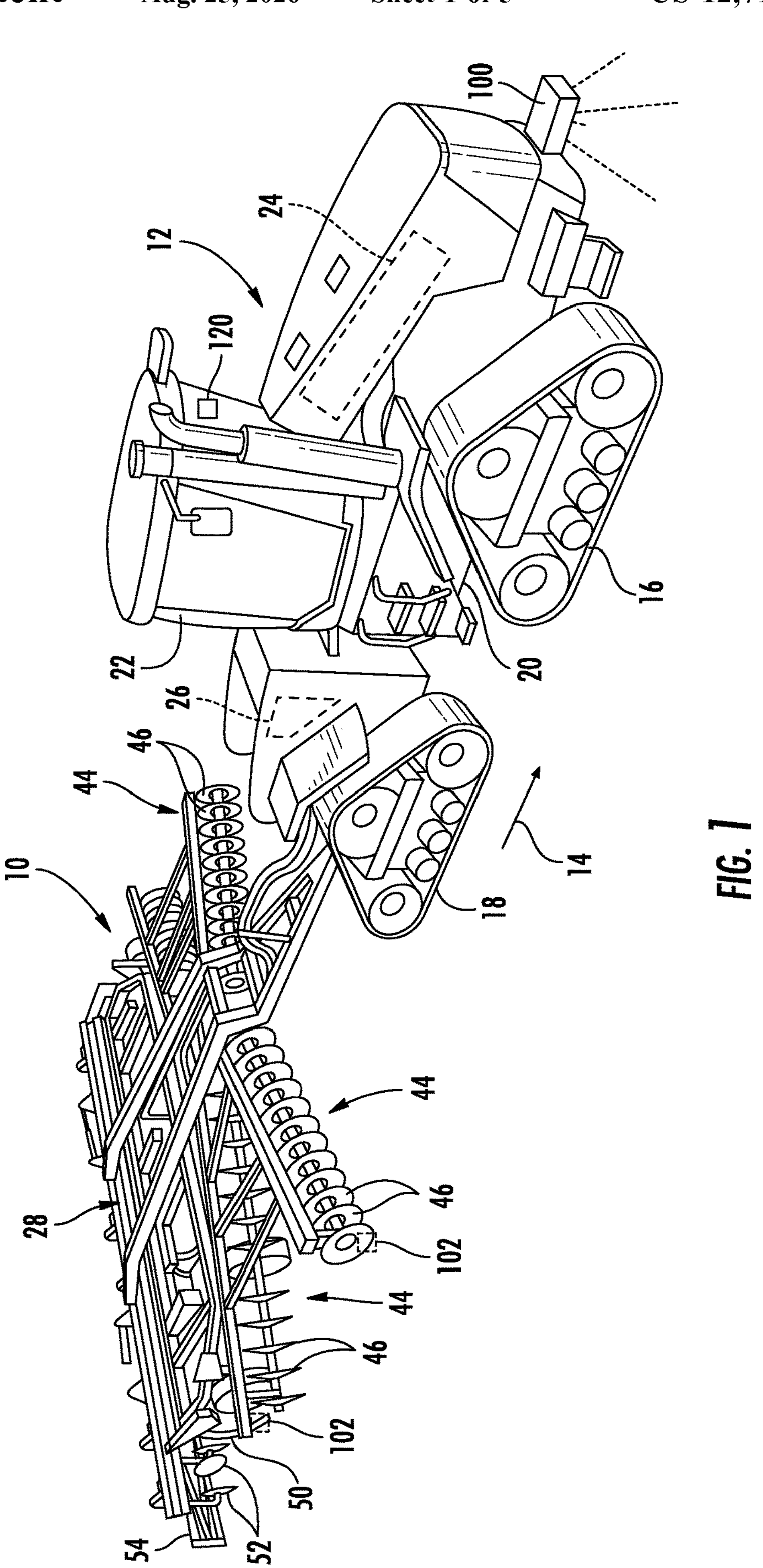
FIG. 1 illustrates a perspective view of one embodiment of a tillage implement coupled to a work vehicle in accordance with aspects of the present subject matter.

Repeat use of reference characters in the present specification and drawings is intended to represent the same or analogous features or elements of the present technology.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to systems and methods for monitoring soil moisture within a field during the performance of an agricultural operation with an agricultural implement. Specifically, in accordance with aspects of the present subject matter, the disclosed system may include a first, non-contact soil moisture sensor (e.g., a GPR sensor) configured to generate non-contact data indicative of soil moisture within the field without contacting the field during an agricultural operation of an agricultural implement. Further, the disclosed system may include a second soil moisture sensor (e.g., a capacitance sensor or reflectance sensor) supported on the agricultural implement, such that the second moisture sensor generates data indicative of the soil moisture within the field during the agricultural operation, where the other soil moisture sensor is of a different type than the non-contact soil moisture sensor. To determine a soil moisture content at a given location within the field based at least in part on the non-contact data, a computing device or controller of the disclosed system may be configured to select a predetermined relationship from a plurality of different predetermined relationships. In general, each of the predetermined relationships is associated with a respective soil type of a plurality of different soil types and usable to determine a soil moisture content for the respective soil type based on the non-contact data, where the selected predetermined relationship is associated with an expected soil type at the given location within the field. The computing device may then determine a first soil moisture content at the given location in the field based at least in part on the selected predetermined relationship and the non-contact data associated with the given location. The computing device may separately determine a second soil moisture content for the given location in the field based at least in part on the data generated by the second moisture sensor. Thereafter, the computing device may determine if the selected predetermined relationship is associated with an actual soil type present at the given location based on the first and second soil moisture contents determined. For instance, if the first and second moisture contents are within a threshold tolerance of each other, the expected soil type is confirmed as the actual soil type present and the selected predetermined relationship is determined to be associated with the actual soil type present at the first location. Otherwise, if the first and second soil moisture contents are not within the threshold tolerance of each other, the expected soil type is not the actual soil type present and the selected predetermined relationship is not associated with the actual soil type present at the first location.

When the selected predetermined relationship is not associated with the actual soil type present at the first location, the computing device may be configured to determine that the actual soil type present at the first location is another soil type, such as the expected soil type present at another location in the field. For instance, the computing device may assume that the actual soil type present is the expected soil type at an adjacent location in the field. Then, the computing device may select another predetermined relationship from the plurality of predetermined relationships that is associated with the expected soil type present at the other location in the field for determining the soil moisture within the field at the first location. As such, with the disclosed system and method, an appropriate predetermined relationship may be selected for the soil type within the field, with which the moisture content within the field may be more accurately determined and monitored from non-contact data (e.g., GPR data), allowing for an improved tillage operation.

Figure 2:
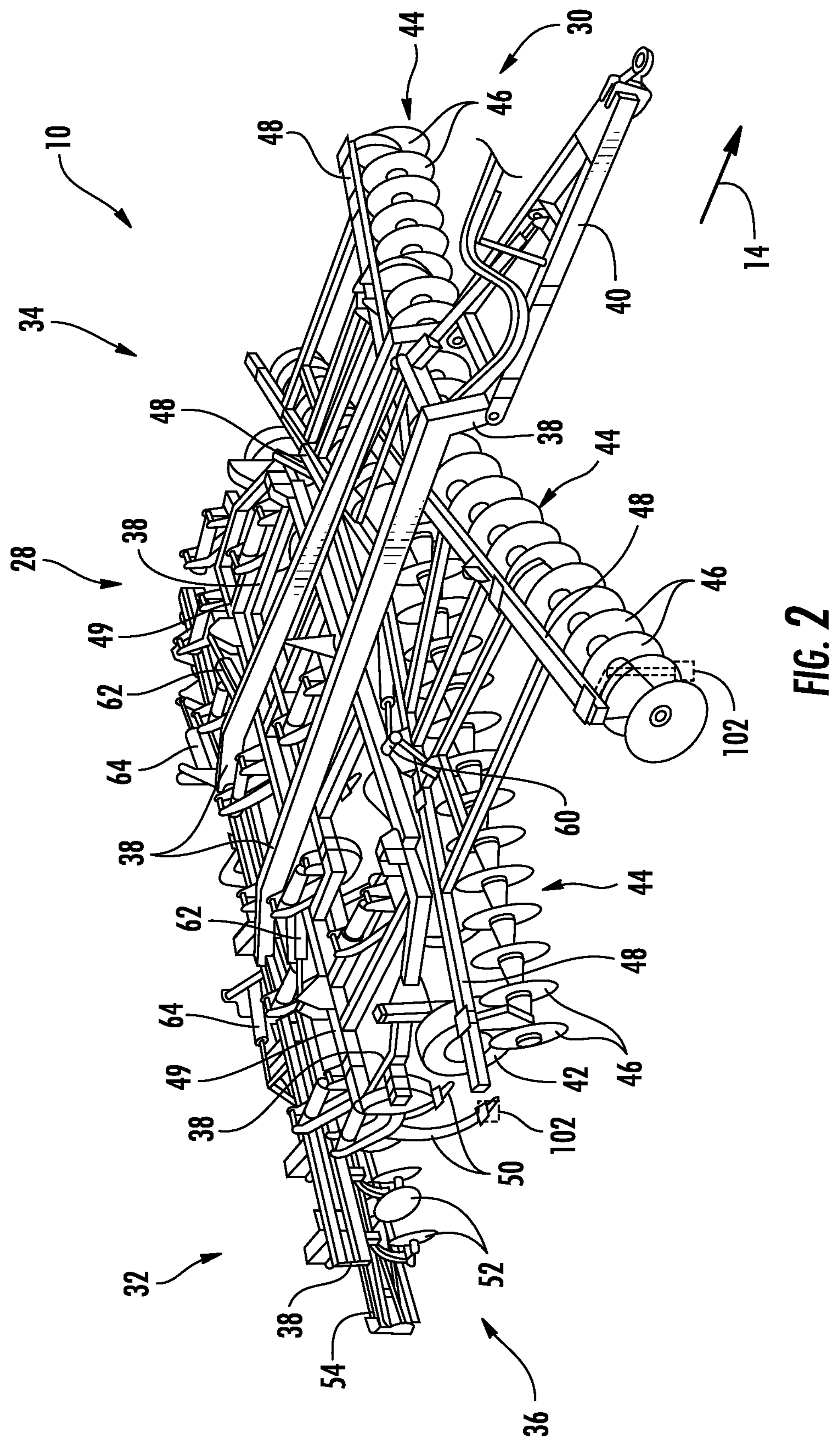
FIG. 2 illustrates another perspective view of the implement, particularly illustrating various components of the implement, in accordance with aspects of the present subject matter.

Referring now to the drawings, FIGS. 1 and 2 illustrate differing perspective views of one embodiment of an agricultural implement 10 in accordance with aspects of the present subject matter. Specifically, FIG. 1 illustrates a perspective view of the agricultural implement 10 coupled to a work vehicle 12. Additionally, FIG. 2 illustrates a perspective view of the implement 10, particularly illustrating various components of the implement 10.

In general, the implement 10 may be configured to be towed across a field in a direction of travel (e.g., as indicated by arrow 14) by the work vehicle 12. As shown, the implement 10 may be configured as a tillage implement, and the work vehicle 12 may be configured as an agricultural tractor. However, in other embodiments, the implement 10 may be configured as any other suitable type of implement, such as a seed-planting implement, a fertilizer-dispensing implement, and/or the like. Similarly, the work vehicle 12 may be configured as any other suitable type of vehicle, such as an agricultural harvester, a self-propelled sprayer, and/or the like.

As shown in FIG. 1, the work vehicle 12 may include a pair of front track assemblies 16, a pair or rear track assemblies 18, and a frame or chassis 20 coupled to and supported by the track assemblies 16, 18. An operator's cab 22 may be supported by a portion of the chassis 20 and may house various input devices (e.g., one or more user interfaces 120) for permitting an operator to control the operation of one or more components of the work vehicle 12 and/or one or more components of the implement 10. Additionally, as is generally understood, the work vehicle 12 may include an engine 24 and a transmission 26 mounted on the chassis 20. The transmission 26 may be operably coupled to the engine 24 and may provide variably adjusted gear ratios for transferring engine power to the track assemblies 16, 18 via a drive axle assembly (not shown) (or via axles if multiple drive axles are employed).

As shown in FIGS. 1 and 2, the implement 10 may include a frame 28. More specifically, as shown in FIG. 2, the frame 28 may extend longitudinally between a forward end 30 and an aft end 32. The frame 28 may also extend laterally between a first side 34 and a second side 36. In this respect, the frame 28 generally includes a plurality of structural frame members 38, such as beams, bars, and/or the like, configured to support or couple to a plurality of components. Furthermore, a hitch assembly 40 may be connected to the frame 28 and configured to couple the implement 10 to the work vehicle 12. Additionally, a plurality of wheels 42 (only one of which is shown in FIG. 2) may be coupled to the frame 28 to facilitate towing the implement 10 in the direction of travel 14.

In several embodiments, one or more ground engaging tools may be coupled to and/or supported by the frame 28. In such embodiments, the ground engaging tool(s) may, for example, include one or more ground-penetrating tools. More particularly, in certain embodiments, the ground engaging tools may include one or more disk blades 46 and/or one or more shanks 50 supported relative to the frame 28. In one embodiment, each disk blade 46 and/or shank 50 may be individually supported relative to the frame 28. Alternatively, one or more groups or sections of the ground engaging tools may be ganged together to form one or more ganged tool assemblies, such as the disk gang assemblies 44 shown in FIGS. 1 and 2.

As illustrated in FIG. 2, each disk gang assembly 44 includes a toolbar 48 coupled to the implement frame 28 and a plurality of disk blades 46 supported by the toolbar 48 relative to the implement frame 28. Each disk blade 46 may, in turn, be configured to penetrate into or otherwise engage the soil as the implement 10 is being pulled through the field. As is generally understood, the various disk gang assemblies 44 may be oriented at an angle relative to the direction of travel 14, such that an axis of rotation of the disks is not perpendicular to the direction of travel 14, to promote more effective tilling of the soil. However, it should be appreciated that the disk gang assemblies 44 may be oriented in any other suitable manner relative to the direction of travel 14. In the embodiment shown in FIGS. 1 and 2, the implement 10 includes four disk gang assemblies 44 supported on the frame 28 at a location forward of the shanks 50, adjacent to the forward end 30 of the implement 10, such as by including two forward disk gang assemblies 44 and two rear disk gang assemblies 44. However, it should be appreciated that, in alternative embodiments, the implement 10 may include any other suitable number of disk gang assemblies 44, such as more or fewer than four disk gang assemblies 44. Furthermore, in one embodiment, the disk gang assemblies 44 may be mounted to the frame 28 at any other suitable location, such as adjacent to aft end 32 of the implement 10.

It should be appreciated that, in addition to the shanks 50 and the disk blades 46, the implement frame 28 may be configured to support any other suitable ground engaging tools. For instance, in the illustrated embodiment, the frame 28 is also configured to support a plurality of leveling blades 52 and rolling (or crumbler) basket assemblies 54.

Moreover, in several embodiments, the implement 10 may include a plurality of actuators configured to adjust the positions of the implement 10 and/or various ground engaging tools coupled thereto. For example, in some embodiments, the implement 10 may include a plurality of disk gang actuators 60 (one is shown in FIG. 2), with each actuator 60 being configured to move or otherwise adjust the orientation or position of one or more of the disk gang assemblies 44 relative to the implement frame 28. For example, a first end of each actuator 60 may be coupled to a toolbar 48 of the corresponding disk gang assembly 44, while a second end of each actuator 60 may be coupled to the frame 28. Each actuator 60 may be configured to extend and/or retract to adjust the angle of the corresponding disk gang assembly(ies) 44 relative to a lateral centerline (not shown) of the frame 28 and/or the penetration depth of the associated disk blades 46. Furthermore, each actuator 60 may be configured to extend and/or retract to adjust a downforce applied by the actuator(s) 60 to the disk gang assembly(ies) 44, and thus the disk blades 46.

Further, in some embodiments, the implement 10 may include a plurality of shank frame actuator(s) 62 (FIG. 2), with each actuator 62 being configured to move or otherwise adjust the orientation or position of one or more of the shanks 50 relative to the implement frame 28. For example, each actuator 62 may be coupled between a toolbar 49 supporting the shank(s) 50 and the implement frame 28. As such the actuator(s) 62 may be configured to extend and/or retract to adjust the position of the toolbar(s) 49 and, thus, a penetration depth of the associated shank(s) 50. Similarly, in some embodiments, the implement 10 may include a plurality of basket actuator(s) 64, with each actuator 64 being configured to move or otherwise adjust the orientation or position of one or more of the basket assemblies 54 relative to the implement frame 28. For example, each actuator 64 may be coupled between one or more of the basket assemblies 54 and the implement frame 28 and be configured to extend and/or retract to adjust an aggressiveness of the associated basket assembly(ies) 54.

In the illustrated embodiment, each actuator 60, 62, 64 corresponds to a fluid-driven actuator, such as a hydraulic or pneumatic cylinder. However, it should be appreciated that each actuator 60, 62, 64 may correspond to any other suitable type of actuator, such as an electric linear actuator. It should additionally be appreciated that the implement 10 may include any other suitable actuators for adjusting the position and/or orientation of the ground-engaging tools of the implement 10 relative to the ground and/or implement frame 28.

In accordance with aspects of the present subject matter, the implement 10 and/or the work vehicle 12 may be equipped with different types of field condition sensors for monitoring field conditions (e.g., soil moisture) within the field during the performance of an agricultural operation with the implement 10. For instance, one or more first sensors 100 and one or more second sensors 102 may be supported on the vehicle 12 and/or on the implement 10, with each of the sensors 100, 102 being configured to generate data indicative of one or more field conditions, particularly data indicative of a moisture content of the field. For example, the first sensor(s) 100 are supported on the vehicle 12 and/or on the implement 10 such that the first sensor(s) 100 are spaced apart from and above a surface of the field during an agricultural operation with the implement 10 while having a field of view generally directed towards a portion of the field. In some embodiments, the field of view of each of the first sensor(s) 100 (also referred to herein as "non-contact sensor(s) 100) is directed towards a portion of the field that has yet to be worked by the implement 10, such that there is sufficient time to process the data generated by the non-contact sensor(s) 100 before the implement 10 passes over the detected area. For instance, the field of view of the sensor(s) 100 may be directed in front of the vehicle 12, in front of the implement 10, and/or towards an adjacent swath to the current swath the implement is currently traveling in that the implement 10 will traverse during a later pass. However, it should be appreciated that, in some embodiments, the non-contact sensor(s) 100 may be mounted on a vehicle configured to perform a separate pass across the field, such as on an unmanned aerial vehicle (UAV) and/or the like, such that the sensor(s) 100 may generate data before and/or during the performance of the agricultural operation with the agricultural implement 10. The non-contact sensor(s) 100 may be any suitable non-contact sensor, such as a ground penetrating radar (GPR) sensor(s). In general, GPR sensors may be operable at multiple frequencies, with each frequency being associated with a different depth beneath the surface of the field, such that GPR data generated by the GPR sensor(s) may be indicative of soil properties (e.g., moisture) at different depths beneath the surface of the field within the field of view of the GPR sensor.

The second sensor(s) 102 are of a different type from the non-contact sensor(s) 100. For instance, the sensor(s) 102 may be any other suitable sensor for generating data indicative of the field condition (e.g., soil moisture) within the field, such as a capacitance sensor or a reflectance sensor. The sensor(s) 102 may be supported on the vehicle 12 and/or on the implement 10 such that the sensor(s) 102 may generate data indicative of the moisture content of the field during the agricultural operation with the implement 10. For instance, depending on the sensor type, the sensor(s) 102 may be positioned in contact with and/or at least partially below a surface of the field during the agricultural operation to determine the soil moisture below the field surface. In some embodiments, the sensor(s) 102 are supported on or coupled to the ground engaging tool(s) 46, 50, 52, 54 of the implement 10. However, in some embodiments, one or more of the sensor(s) 102 may be supported on the implement 10, independently of the ground engaging tool(s) 46, 50, 52, 54 and/or may be supported on the vehicle 12. In one embodiment, the sensor(s) 102 are supported at the front end of the implement 10 (e.g., on the forward-most ground engaging tool(s)) and/or on the vehicle 12 such that soil moisture within the field at a given location may be determined before the implement 10 has finished passing over the given location based on the data generated by the sensor(s) 102.

As will be described in greater detail below, the data from the non-contact sensor(s) 100 is generally dependent on the soil type within the field. For instance, the non-contact data for a portion of a field with one soil type may be different from a portion of the field having another soil type, even when a field condition (e.g., soil moisture) is the same between the two portions of the field. As such, the field condition (e.g., soil moisture) for a given location determined based on data from the second sensor(s) 102 may be used to determine whether an expected soil type at the given location is the actual soil type at the given location, and thus, whether the field condition (e.g., soil moisture) determined based on the expected soil type at the given location and the non-contact data generated by the non-contact sensor(s) 100 is accurate.

It should be appreciated that the configuration of the implement 10 described above and shown in FIGS. 1 and 2 and the work vehicle 12 described above and shown in FIG. 1 is provided only to place the present subject matter in an exemplary field of use. Thus, it should be appreciated that the present subject matter may be readily adaptable to any manner of implement and work vehicle configuration.

Figure 3:
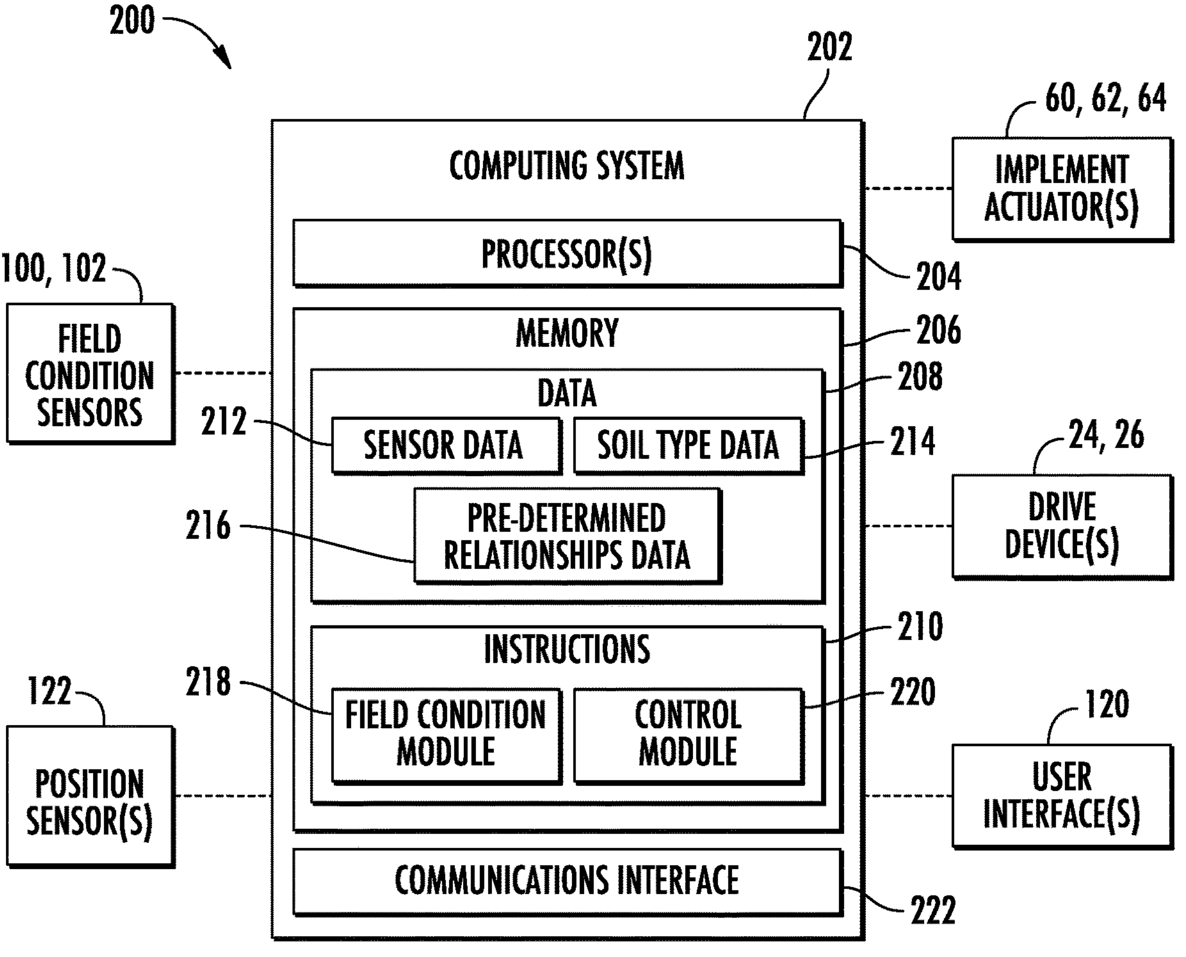
FIG. 3 illustrates a schematic view of a system for monitoring soil moisture within a field during the performance of agricultural operation with an agricultural implement in accordance with aspects of the present subject matter.

Referring now to FIG. 3, a schematic view is illustrated of one embodiment of a system 200 for monitoring soil moisture within a field during the performance of an agricultural operation with an agricultural implement. In general, the system 200 will be described herein with reference to the implement 10 and vehicle 12 described above with reference to FIGS. 1 and 2. However, it should be appreciated that the disclosed system 200 may generally be utilized with any other suitable implement/vehicle combination having any other suitable implement/vehicle configuration. Additionally, it should be appreciated that, for purposes of illustration, communicative links or electrical couplings of the system 200 shown in FIG. 3 are indicated by dashed lines.

In several embodiments, the system 200 may include a computing system 202 and various other components configured to be communicatively coupled to and/or controlled by the computing system 202, such as the field condition sensors 100, 102 configured to capture field condition data indicative of field conditions (e.g., soil moisture) within the field, actuator(s) of the implement 10 (e.g., implement actuator(s) 60, 62, 64), drive device(s) of the vehicle 12 (e.g., engine 24, transmission 26, etc.), and/or a user interface(s) (e.g., user interface(s) 120). The user interface(s) 120 described herein may include, without limitation, any combination of input and/or output devices that allow an operator to provide operator inputs to the computing system 202 and/or that allow the computing system 202 to provide feedback to the operator, such as a keyboard, keypad, pointing device, buttons, knobs, touch sensitive screen, mobile device, audio input device, audio output device, and/or the like. Additionally, the computing system 202 may be communicatively coupled to one or more position sensors 122 configured to generate data indicative of the location of the implement 10 and/or the vehicle 12, such as a satellite navigation positioning device (e.g., a GPS system, a Galileo positioning system, a Global Navigation satellite system (GLONASS), a BeiDou Satellite Navigation and Positioning system, a dead reckoning device, and/or the like).

In general, the computing system 202 may correspond to any suitable processor-based device(s), such as a computing device or any combination of computing devices. Thus, as shown in FIG. 3, the computing system 202 may generally include one or more processor(s) 204 and associated memory devices 206 configured to perform a variety of computer-implemented functions (e.g., performing the methods, steps, algorithms, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory 206 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory 206 may generally be configured to store information accessible to the processor (s) 204, including data 208 that can be retrieved, manipulated, created and/or stored by the processor(s) 204 and instructions 210 that can be executed by the processor(s) 204.

It should be appreciated that the computing system 202 may correspond to an existing computing device for the implement 10 or the vehicle 12 or may correspond to a separate processing device. For instance, in one embodiment, the computing system 202 may form all or part of a separate plug-in module that may be installed in operative association with the implement 10 or the vehicle 12 to allow for the disclosed system and method to be implemented without requiring additional software to be uploaded onto existing control devices of the implement 10 or the vehicle 12.

In several embodiments, the data 208 may be stored in one or more databases. For example, the memory 206 may include a sensor database 212 for storing data generated by the sensors 100, 102, 122. For instance, the non-contact sensor(s) 100 may be configured to continuously or periodically capture data associated with a portion of the field, such as before or during the performance of the agricultural operation with the implement 10. Similarly, the sensor(s) 102 may be configured to continuously or periodically capture data associated with a portion of the field, such as before or during the performance of the agricultural operation with the implement 10. Additionally, the data from the sensors 100, 102 may be taken with reference to the position of the implement 10 and/or the vehicle 12 within the field based on the position data from the position sensor(s) 122. The data transmitted to the computing system 202 from the sensors 100, 102, 122 may be stored within the sensor database 212 for subsequent processing and/or analysis. It should be appreciated that, as used herein, the term sensor data 212 may include any suitable type of data received from the sensor 100, 102, 122 that allows for the field conditions (e.g., moisture) of a field to be analyzed, including GPR data, capacitance data, reflectance data, GPS coordinates, and/or other suitable type of data.

Figure 4:
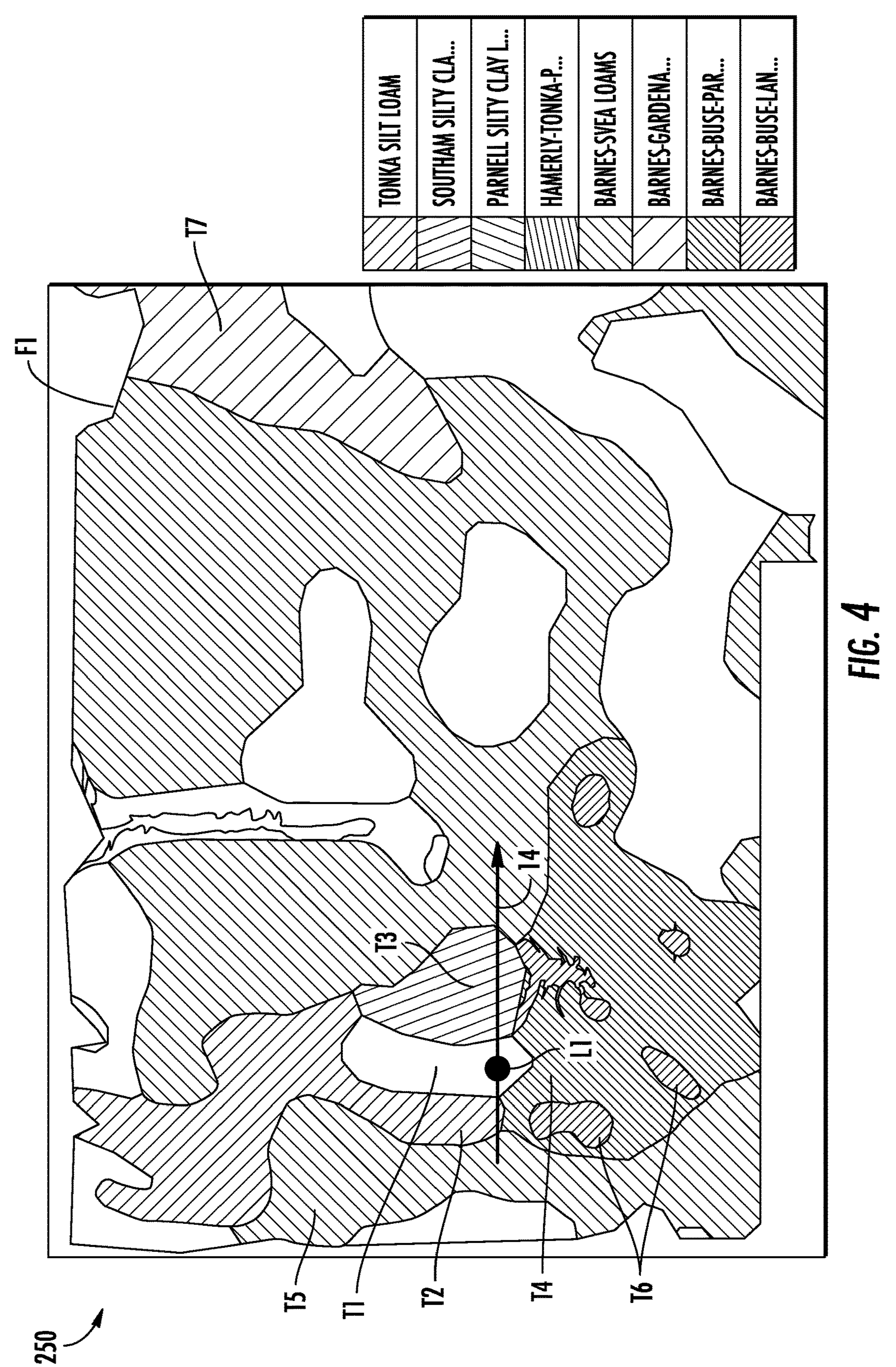
FIG. 4 illustrates an example soil type map for use when monitoring soil moisture within a field during the performance of agricultural operation with an agricultural implement in accordance with aspects of the present subject matter.

Moreover, in some embodiments, the memory 206 may also include a soil type database 214 for storing field data indicative of the different soil types across a field. The field data stored in the soil type database 214 may include, for example, a soil type map indicating the soil type (e.g., established composition of silt, loam, clay, sand, etc., and/or texture) at each location within a field. For instance, FIG. 4 illustrates an example soil type map 250 that indicates the soil type (e.g., a first soil type T1, a second soil type T2, a third soil type T3, a fourth soil type T4, a fifth soil type T5, a sixth soil type T6, a seventh soil type T7, etc.) at each location in a field F1. The field data stored in the soil type database 214 may be generated and stored in the soil type database 214 before the performance of the agricultural operation with the agricultural implement 10. Soil type maps may be, for example, SSURGO maps, and/or any other suitable type of soil map. However, it should be appreciated that the field data may be stored in any other suitable format other than a soil type map, such as a lookup table, and/or the like.

Referring still to FIG. 3, in some embodiments, the memory 206 may additionally include a predetermined relationships database 216 for storing predetermined relationships for analyzing the sensor data 212. More particularly, as indicated above, the data generated by the non-contact sensor(s) 100 may be at least partially dependent on the soil type within the field of view of the sensor(s) 100. As such, a plurality of predetermined relationships may be stored in the predetermined relationships database 216, where each of the plurality of predetermined relationships is associated with determining a field condition (e.g., moisture content) for a respective soil type of a plurality of soil types (e.g., the soil types T1, T2, T3, T4, T5, T6, T7, etc.) based at least in part on the non-contact data from the sensor(s) 100. For instance, the plurality of predetermined relationships may include look-up tables, suitable mathematical formulas, and/or algorithms stored in the predetermined relationships database 216 that correlates the data from the non-contact sensor(s) 100 to the field condition (e.g., moisture content) for the particular soil type.

The instructions 210 stored within the memory 206 of the computing system 202 may be executed by the processor(s) 204 to implement a field condition module 218. In general, the field condition module 218 may be configured to assess the sensor data 212 deriving from the sensors 100, 102, 122 to determine a field condition (e.g., moisture content) across the field. For instance, as indicated above, in one embodiment, data may be captured by the field condition sensor(s) 100, 102 indicative of a field condition (e.g., moisture content) at a given location in the field, where the given location in the field may be determined from position data generated by the position sensor(s) 122. The field condition module 218 may be configured to determine an expected soil type at the given location in the field based at least in part on the data stored in the soil type database 214. For example, the field condition module 218 may determine the expected soil type as being the first soil type T1 for a first location L1 within the field F1 from the soil type map 250 in FIG. 4. As such, the field condition module 218 may then select a first predetermined relationship from the plurality of predetermined relationships in the predetermined relationships database 216, where the first predetermined relationship corresponds to the expected soil type (e.g., the first soil type T1).

Thereafter, the field condition module 218 may determine a first field characteristic value (e.g., a first soil moisture content) of the field at the given location (e.g., location L1) based on the selected first predetermined relationship and the data generated by the non-contact sensor(s) 100. Separately, the field condition module 218 may determine a second field characteristic value (e.g., a second soil moisture content) of the field at the given location (e.g., location L1) based on the data generated by the sensor(s) 102. For instance, the field condition module 218 may use any known correlation (e.g., look-up tables, suitable mathematical formulas, and/or algorithms) between the data generated by the sensor(s) 102 and soil moisture content to determine the second soil moisture content. Such known correlations may also be stored within the predetermined relationships database 216, or otherwise be accessible to the field condition module 218.

The field condition module 218 may then be configured to determine whether the first predetermined relationship is associated with an actual soil type at the given location. For instance, the field condition module 218 may compare the first and second soil moisture contents. For example, if a difference between the first and second soil moisture contents is less than a threshold difference, then the first predetermined relationship is associated with the actual soil type at the given location, and the first soil moisture content determined is accurate. Conversely, if a difference between the first and second soil moisture contents is greater than the threshold difference, then the first predetermined relationship is not associated with the actual soil type at the given location, and the first soil moisture content determined is not accurate enough. The threshold difference may be approximately 10% of the second soil moisture content.

If it is determined that the first predetermined relationship is not associated with an actual soil type at the given location, the field condition module 218 may assume that another soil type present within the field that the implement 10 encounters is the actual soil type at the given location. For example, in one embodiment, the field condition module 218 may assume that one of the other soil types (e.g., one of the soil types T2, T3, T4, T5, T6, T7) associated with a different location in the field from the given location is the updated, expected soil type. In some embodiments, the field condition module 218 may determine that the soil type adjacent the given location in the field may be the updated, expected soil type. For example, as shown in FIG. 4, the second soil type T2, the third soil type T3, and the fourth soil type T4 are all soil types directly adjacent the first location L1, thus, one of second soil type T2, the third soil type T3, or the fourth soil type T4 may be the updated expected soil type. In one embodiment, the field condition module 218 may determine that a previous soil type encountered or a next soil type to be encountered may be the expected soil type. For example, as shown in FIG. 4, the updated expected soil type may be one of the previous soil type (e.g., the second soil type T2) or the next soil type (e.g., the third soil type T3) along the direction of travel 14 from the first location L1.

Once the updated, expected soil type is determined, the field condition module 218 may be configured to select another predetermined relationship (e.g., a second predetermined relationship) from the plurality of predetermined relationships stored in the predetermined relationships database 216, where the other predetermined relationship is associated with the updated, expected soil type at the given location. In some embodiments, the field condition module 218 may determine a third field characteristic value (e.g., a third soil moisture content) of the field at the given location (e.g., location L1) based on the selected second predetermined relationship and the data generated by the non-contact sensor(s) 100. Thereafter, the field condition module 218 may determine whether the selected second predetermined relationship is associated with the actual soil type at the given location. For instance, the field condition module 218 may compare the second and third soil moisture contents. For example, if a difference between the second and third soil moisture contents is less than the threshold difference, then the second predetermined relationship is associated with the actual soil type at the given location, and the third soil moisture content is accurate. Conversely, if a difference between the second and third soil moisture contents is greater than the threshold difference, then the second predetermined relationship is also not associated with the actual soil type at the given location, and a further predetermined relationship may be selected from the plurality of predetermined relationships stored in the predetermined relationships database 216.

It should be appreciated that, in some embodiments, the described comparison of the moisture contents determined based on data generated by the different sensors 100, 102 to confirm that the correct predetermined relationship is being used with the data from the sensor(s) 100 may take place continuously, periodically (e.g., at a given time and/or distance interval, etc.), selectively, or when certain conditions are met during an agricultural operation with the implement 10. For instance, in some embodiments, the comparison of the moisture contents only takes place near expected transitions in the field between expected soil types. For example, if the soil type data 214 indicates that a given location is within a certain range (e.g., within a resolution error of the soil type data 214, such as within 3 meters, 2 meters, 1 meter, and/or the like) of more than one soil type, the comparison between moisture contents determined based on data from the different sensors 100, 102 may be performed. Similarly, in some embodiments, the comparison of the moisture contents takes place before and/or after a headland turn. Further, in some embodiments, the comparison is performed when requested by an operator (e.g., via the user interface(s) 120).

By confirming that the correct predetermined relationship is being used to determine field conditions (e.g., soil moisture) from the data generated by the sensor(s) 100, the soil moisture may be accurately monitored using non-contact sensor(s) 100.

It should additionally be appreciated that, in some embodiments, the field condition module 218 may also be configured to control the sensor(s) 100 to generate data. More particularly, the field condition module 218 may also be configured to control the sensor(s) 100, when the sensor (s) 100 are GPR sensors, to operate at a plurality of frequencies, such that the data generated by the sensor(s) 100 is indicative of the field condition (e.g., moisture content) of the field at a plurality of depths, each of the plurality of depths being associated with one of the plurality of frequencies.

Referring still to FIG. 3, in some embodiments, the instructions 210 stored within the memory 206 of the computing system 202 may also be executed by the processor(s) 204 to implement a control module 220. The control module 220 may generally be configured to initiate or perform a control action based on the monitored field conditions. The control action, in one embodiment, includes adjusting the operation of one or more components of the implement 10, such as adjusting the operation of one or more of the actuators 60, 62, 64 to adjust the penetration depth of the ground engaging tool(s) 46, 50, 52, 54 and/or adjust the operation of one or more of the drive device(s) 24, 26 to adjust a speed of the implement 10 and/or the vehicle 12 based on the monitored field conditions (e.g., soil moisture) to improve performance of the implement 10 (e.g., prevent plugging and/or compaction). In some embodiments, the control action may include controlling the operation of the user interface 120 to notify an operator of the field conditions (e.g., soil moisture), and/or the like. Additionally, or alternatively, in some embodiments, the control action may include adjusting the operation of the implement 10 based on an input from an operator, e.g., via the user interface 120.

Additionally, as shown in FIG. 3, the computing system 202 may also include a communications interface 222 to provide a means for the computing system 202 to communicate with any of the various other system components described herein. For instance, one or more communicative links or interfaces (e.g., one or more data buses) may be provided between the communications interface 222 and the sensor(s) 100, 102, 122 to allow data transmitted from the sensor(s) 100, 102, 122 to be received by the computing system 202. Similarly, one or more communicative links or interfaces (e.g., one or more data buses) may be provided between the communications interface 222 and the user interface 120 to allow operator inputs to be received by the computing system 202 and to allow the computing system 202 to control the operation of one or more components of the user interface 120. Moreover, one or more communicative links or interfaces (e.g., one or more data buses) may be provided between the communications interface 222 and the implement actuator(s) 60, 62, 64 and/or the drive device(s) 24, 26 to allow the computing system 202 to control the operation of one or more components of the implement actuator(s) 60, 62, 64 and/or the drive device(s) 24, 26.

Figure 5:
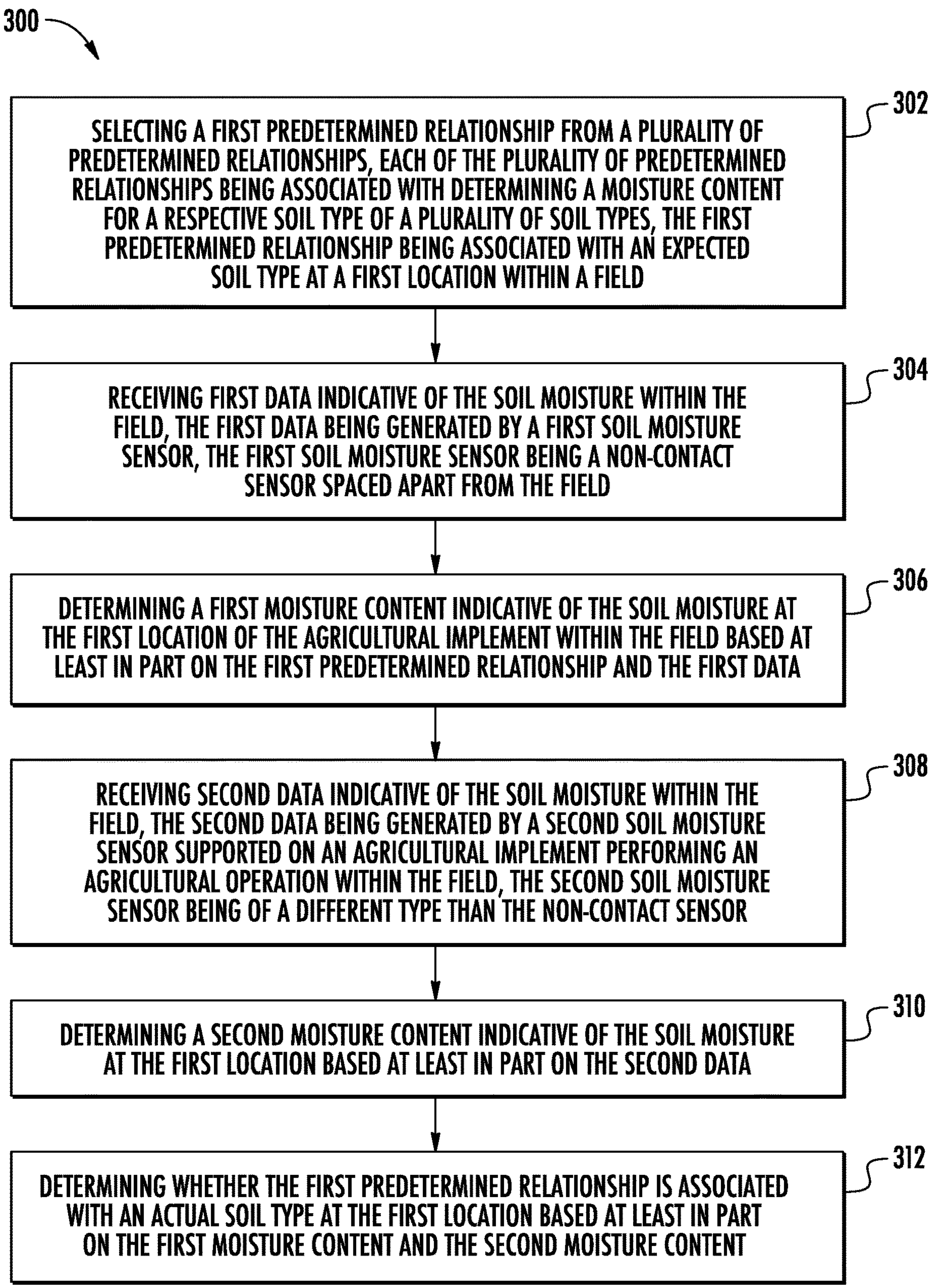
FIG. 5 illustrates a flow diagram of one embodiment of a method for monitoring soil moisture within a field during the performance of agricultural operation with an agricultural implement in accordance with aspects of the present subject matter.

Referring now to FIG. 5, a flow diagram of one embodiment of a method 300 for monitoring soil moisture within a field during the performance of agricultural operation with an agricultural implement is illustrated in accordance with aspects of the present subject matter. In general, the method 300 will be described herein with reference to the implement 10 and the work vehicle 12 shown in FIGS. 1-2, as well as the various system components shown in FIG. 3. However, it should be appreciated that the disclosed method 300 may be implemented with work vehicles and/or implements having any other suitable configurations, and/or within systems having any other suitable system configuration. In addition, although FIG. 5 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 5, at (302), the method 300 may include selecting a first predetermined relationship from a plurality of predetermined relationships, each of the plurality of predetermined relationships being associated with determining a moisture content for a respective soil type of a plurality of soil types, the first predetermined relationship being associated with an expected soil type at a first location within a field. For instance, as discussed above, the computing system 202 may select a first predetermined relationship from a plurality of predetermined relationships (e.g., stored in the predetermined relationships database 216), where each of the plurality of predetermined relationships is associated with determining a field condition (e.g., moisture content) for a respective soil type of a plurality of soil types, the first predetermined relationship being associated with an expected soil type at a first location within a field (e.g., associated with the first soil type T1 at the first location L1 within the field F1).

At (304), the method 300 may further include receiving first data indicative of the soil moisture within the field, the first data being generated by a first soil moisture sensor, the first soil moisture sensor being a non-contact sensor spaced apart from the field. For instance, as discussed above, the computing system 202 may receive first data indicative of the field condition (e.g., soil moisture) within the field, the first data being generated by a first soil moisture sensor, particularly the non-contact sensor(s) 100 being spaced apart from the field during the data generation.

Further, at (306), the method 300 may include determining a first moisture content indicative of the soil moisture at the first location of the agricultural implement within the field based at least in part on the first predetermined relationship and the first data. For example, as described above, the computing system 202 may determine a first moisture content indicative of the soil moisture at the first location (e.g., first location L1) based at least in part on the selected, first predetermined relationship and the first data generated by the non-contact sensor(s) 100 associated with the first location.

Furthermore, at (308), the method 300 may include receiving second data indicative of the soil moisture within the field, the second data being generated by a second soil moisture sensor supported on an agricultural implement performing an agricultural operation within the field, the second soil moisture sensor being of a different type than the non-contact sensor. For instance, as discussed above, the computing system 202 may receive second data indicative of the soil moisture within the field, where the second data is generated by a second soil moisture sensor (e.g., sensor(s) 102) supported on the agricultural implement 10 performing the agricultural operation within the field and/or the vehicle 12 towing the implement 10, where the second soil moisture sensor is of a different type (e.g., a capacitance sensor, a reflectance sensor, etc.) than the non-contact sensor (which is for example, a GPR sensor).

Moreover, at (310), the method 300 may include determining a second moisture content indicative of the soil moisture at the first location based at least in part on the second data. For example, as described above, the computing system 202 may be configured to determine a second moisture content indicative of the soil moisture at the first location based at least in part on the second data generated by the sensor(s) 102, where the second data is associated with the first location within the field.

Additionally, at (312), the method 300 may include determining whether the first predetermined relationship is associated with an actual soil type at the first location based at least in part on the first moisture content and the second moisture content. For instance, as discussed above, the computing system 202 may determine whether the first predetermined relationship is associated with an actual soil type at the first location based at least in part on the first moisture content (determined based at least in part on the data generated by the non-contact sensor(s) 100) and the second moisture content (determined based at least in part on the data generated by the sensor(s) 102). For example, the computing system 202 may compare a difference between the first and second moisture contents to a threshold difference, if the difference is less than the threshold difference, then the first predetermined relationship is associated with an actual soil type at the first location, otherwise, the first predetermined relationship is not associated with an actual soil type at the first location.

It is to be understood that the steps of the method 300 are performed by the computing system 202 upon loading and executing software code or instructions which are tangibly stored on a tangible computer readable medium, such as on a magnetic medium, e.g., a computer hard drive, an optical medium, e.g., an optical disk, solid-state memory, e.g., flash memory, or other storage media known in the art. Thus, any of the functionality performed by the computing system 202 described herein, such as the method 300, is implemented in software code or instructions which are tangibly stored on a tangible computer readable medium. The computing system 202 loads the software code or instructions via a direct interface with the computer readable medium or via a wired and/or wireless network. Upon loading and executing such software code or instructions by the computing system 202, the computing system 202 may perform any of the functionality of the computing system 202 described herein, including any steps of the method 300 described herein.

The term "software code" or "code" used herein refers to any instructions or set of instructions that influence the operation of a computer or computing system. They may exist in a computer-executable form, such as machine code, which is the set of instructions and data directly executed by a computer's central processing unit or by a computing system, a human-understandable form, such as source code, which may be compiled in order to be executed by a computer's central processing unit or by a computing system, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a computing system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An agricultural system for monitoring soil moisture within a field during a performance of an agricultural operation with an agricultural implement, comprising:

a first soil moisture sensor configured to generate first data indicative of soil moisture within the field, the first soil moisture sensor being a non-contact sensor spaced apart from the field during the agricultural operation;

a second soil moisture sensor configured to generate second data indicative of soil moisture within the field, the second soil moisture sensor being supported on the agricultural implement, the second soil moisture sensor being of a different sensor type from the first soil moisture sensor; and a computing system communicatively coupled to the first and second soil moisture sensors, the computing system being configured to:

select a first predetermined relationship from a plurality of predetermined relationships, each of the plurality of predetermined relationships being associated with determining a moisture content for a respective soil type of a plurality of soil types, the first predetermined relationship being associated with an expected soil type at a first location within the field;

determine a first moisture content indicative of the soil moisture at the first location based at least in part on the first data and the first predetermined relationship;

determine a second moisture content indicative of the soil moisture at the first location based at least in part on the second data;

determine whether the first predetermined relationship is associated with an actual soil type at the first location by:

comparing the first moisture content and the second moisture content; and determining whether the actual soil type at the first location in the field is different from the expected soil type based on the comparing of the first moisture content and the second moisture content; and initiate a control action associated with the agricultural implement based at least in part on the first moisture content and the second moisture content, the control action comprising at least one of controlling an implement actuator to adjust a penetration depth of a ground-engaging tool of the agricultural implement, controlling a drive device to adjust a speed of the agricultural implement, or controlling a user interface to indicate whether the actual soil type at the first location in the field is different from the expected soil type.

2. The agricultural system of claim 1, wherein determining whether the first predetermined relationship is associated with the actual soil type at the first location comprises:

comparing a difference between the first and second moisture contents to a threshold difference; and determining that the actual soil type at the first location in the field is different from the expected soil type when the difference is greater than the threshold difference.

3. The agricultural system of claim 1, wherein, when the first predetermined relationship is not associated with the actual soil type at the first location, the computing system is further configured to:

determine a different soil type of the plurality of soil types that the agricultural implement encounters at a different location in the field from the first location; and select a second predetermined relationship from the plurality of predetermined relationships based at least in part on the different soil type.

4. The agricultural system of claim 3, wherein the computing system is further configured to:

determine a third moisture content indicative of the soil moisture at the first location based at least in part on the first data and the second predetermined relationship; and determine, when a difference between the third moisture content and the second moisture content for the first location is less than a threshold difference, that the actual soil type of the field at the first location is the different soil type.

5. The agricultural system of claim 1, wherein the first soil moisture sensor comprises a ground-penetrating radar (GPR) supported on one or both of the agricultural implement or a work vehicle towing the agricultural implement.

6. The agricultural system of claim 5, wherein the GPR is configured to operate at a plurality of frequencies, the first data being indicative of the moisture content of the field at a plurality of depths, each of the plurality of depths being associated with one of the plurality of frequencies.

7. The agricultural system of claim 1, wherein the second soil moisture sensor comprises at least one of a capacitance sensor or a reflectance sensor.

8. The agricultural system of claim 1, wherein the second soil moisture sensor is below a surface of the field during the agricultural operation.

9. The agricultural system of claim 1, wherein the computing system is further configured to:

receive field data indicative of the expected soil type at each of a plurality of locations within the field, the field data being generated before the performance of the agricultural operation; and determine the expected soil type at the first location of the agricultural implement within the field based at least in part on the field data.

10. An agricultural method for monitoring soil moisture within a field during a performance of an agricultural operation with an agricultural implement, comprising:

selecting, with a computing system, a first predetermined relationship from a plurality of predetermined relationships, each of the plurality of predetermined relationships being associated with determining a moisture content for a respective soil type of a plurality of soil types, the first predetermined relationship being associated with an expected soil type at a first location within the field;

receiving, with the computing system, first data indicative of the soil moisture within the field, the first data being generated by a first soil moisture sensor, the first soil moisture sensor being a non-contact sensor spaced apart from the field;

determining, with the computing system, a first moisture content indicative of the soil moisture at the first location of the agricultural implement within the field based at least in part on the first predetermined relationship and the first data;

receiving, with the computing system, second data indicative of the soil moisture within the field, the second data being generated by a second soil moisture sensor supported on the agricultural implement, the second soil moisture sensor being of a different sensor type from the first soil moisture sensor;

determining, with the computing system, a second moisture content indicative of the soil moisture at the first location based at least in part on the second data;

determining, with the computing system, whether the first predetermined relationship is associated with an actual soil type at the first location by:

comparing the first moisture content and the second moisture content; and determining whether the actual soil type at the first location in the field is different from the expected soil type based on the comparing of the first moisture content and the second moisture content; and initiating, with the computing system, a control action associated with the agricultural implement based at least in part on the first moisture content and the second moisture content, the control action comprising at least one of controlling an implement actuator to adjust a penetration depth of a ground-engaging tool of the agricultural implement, controlling a drive device to adjust a speed of the agricultural implement, or controlling a user interface to indicate whether the actual soil type at the first location in the field is different from the expected soil type.

11. The agricultural method of claim 10, wherein determining whether the first predetermined relationship is associated with the actual soil type at the first location comprises:

comparing, with the computing system, a difference between the first and second moisture contents to a threshold difference; and determining that the actual soil type at the first location in the field is different from the expected soil type when the difference is greater than the threshold difference.

12. The agricultural method of claim 10, further comprising, when the first predetermined relationship is not associated with the actual soil type at the first location:

determining, with the computing system, a different soil type of the plurality of soil types that the agricultural implement encounters at a different location in the field from the first location;

selecting, with the computing system, a second predetermined relationship from the plurality of predetermined relationships based at least in part on the different soil type; and determining, with the computing system, a third moisture content indicative of the soil moisture at the first location based at least in part on the first data and the second predetermined relationship.

13. The agricultural method of claim 10, wherein the first soil moisture sensor comprises a ground-penetrating radar (GPR), the method further comprising:

controlling, with the computing system, the GPR to operate at a plurality of frequencies, the first data being indicative of the moisture content of the field at a plurality of depths, each of the plurality of depths being associated with one of the plurality of frequencies.

14. The agricultural method of claim 10, wherein the second soil moisture sensor comprises at least one of a capacitance sensor or a reflectance sensor.

15. The agricultural method of claim 10, further comprising:

receiving, with the computing system, field data indicative of the expected soil type at each of a plurality of locations within the field, the field data being generated before the performance of the agricultural operation; and determining, with the computing system, the expected soil type at the first location of the agricultural implement within the field based at least in part on the field data.

* * * * *